(12) United States Patent
Kuzma et al.

(10) Patent No.: US 8,646,172 B2
(45) Date of Patent: Feb. 11, 2014

(54) ELECTRODE ARRAY ASSEMBLY AND METHOD OF MAKING SAME

(75) Inventors: Janusz A. Kuzma, Parker, CO (US); Anne M. Pianca, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 315 days.

(21) Appl. No.: 13/013,599

(22) Filed: Jan. 25, 2011

(65) Prior Publication Data

US 2011/0118815 A1    May 19, 2011

Related U.S. Application Data

(63) Continuation of application No. 11/329,907, filed on Jan. 11, 2006, now Pat. No. 7,891,085.

(60) Provisional application No. 60/643,093, filed on Jan. 11, 2005.

(51) Int. Cl.
*H01R 43/00* (2006.01)
*A61N 1/00* (2006.01)

(52) U.S. Cl.
USPC .......................................... 29/825; 607/116

(58) Field of Classification Search
USPC ................................ 29/825; 607/115–122
See application file for complete search history.

(56) References Cited

U.S. PATENT DOCUMENTS

| | | | | |
|---|---|---|---|---|
| 3,769,984 A | * | 11/1973 | Muench | 607/122 |
| 5,410,797 A | * | 5/1995 | Steinke et al. | 29/435 |
| 5,555,618 A | * | 9/1996 | Winkler | 29/825 |
| 6,055,456 A | * | 4/2000 | Gerber | 607/117 |
| 6,205,361 B1 | * | 3/2001 | Kuzma et al. | 607/116 |
| 6,216,045 B1 | * | 4/2001 | Black et al. | 607/122 |
| 6,249,708 B1 | * | 6/2001 | Nelson et al. | 607/122 |
| 6,551,302 B1 | * | 4/2003 | Rosinko et al. | 604/505 |
| 6,598,280 B1 | * | 7/2003 | Giba et al. | 29/447 |
| 6,909,918 B2 | * | 6/2005 | Stypulkowski | 607/117 |
| 7,047,081 B2 | * | 5/2006 | Kuzma | 607/115 |
| 7,184,840 B2 | * | 2/2007 | Stolz et al. | 607/122 |
| 2004/0024440 A1 | * | 2/2004 | Cole | 607/122 |
| 2004/0225175 A1 | * | 11/2004 | Moody et al. | 600/3 |

(Continued)

OTHER PUBLICATIONS

U.S. Appl. No. 11/329,907, Official Communication mailed Nov. 17, 2008.
U.S. Appl. No. 11/329,907, Official Communication mailed Apr. 2, 2009.
U.S. Appl. No. 11/329,907, Official Communication mailed Jul. 1, 2009.
U.S. Appl. No. 11/329,907, Official Communication mailed Mar. 31, 2010.
U.S. Appl. No. 11/329,907, Notice of Allowance mailed Nov. 15, 2010.

*Primary Examiner* — David Angwin
(74) *Attorney, Agent, or Firm* — Frommer Lawrence & Haug LLP; Bruce E. Black

(57) ABSTRACT

A method of manufacturing a stimulation lead includes providing a lead body having an insulation section that defines a central lumen extending along the insulation section and conductor lumens extending along the insulation section and arranged around, and external to, the central lumen. The lead body also includes conductive contacts located along an axial end of the lead body and conductor wires with each conductor wire disposed within one of the conductor lumens and each of the conductor lumens having at least one of the conductor wires disposed therein. After providing the lead body, conductively at least one of the conductor wires to each of the conductive contacts; and placing non-conductive material into a portion of at least one of the conductor lumens of the lead body. A portion of the conductor lumens and at least a portion of the non-conductive material are disposed radially beneath the conductive contacts.

11 Claims, 6 Drawing Sheets

(56) References Cited

U.S. PATENT DOCUMENTS

| | | |
|---|---|---|
| 2005/0215945 A1* | 9/2005 | Harris et al. .................... 604/66 |
| 2006/0036218 A1* | 2/2006 | Goodson et al. .............. 604/264 |
| 2007/0021771 A1* | 1/2007 | Oepen et al. .................. 606/194 |
| 2007/0021821 A1* | 1/2007 | Johnson et al. .............. 623/1.11 |
| 2007/0249997 A1* | 10/2007 | Goodson et al. ........... 604/93.01 |
| 2008/0097426 A1* | 4/2008 | Root et al. ....................... 606/41 |
| 2009/0018487 A1* | 1/2009 | Doty ............................... 604/21 |

* cited by examiner

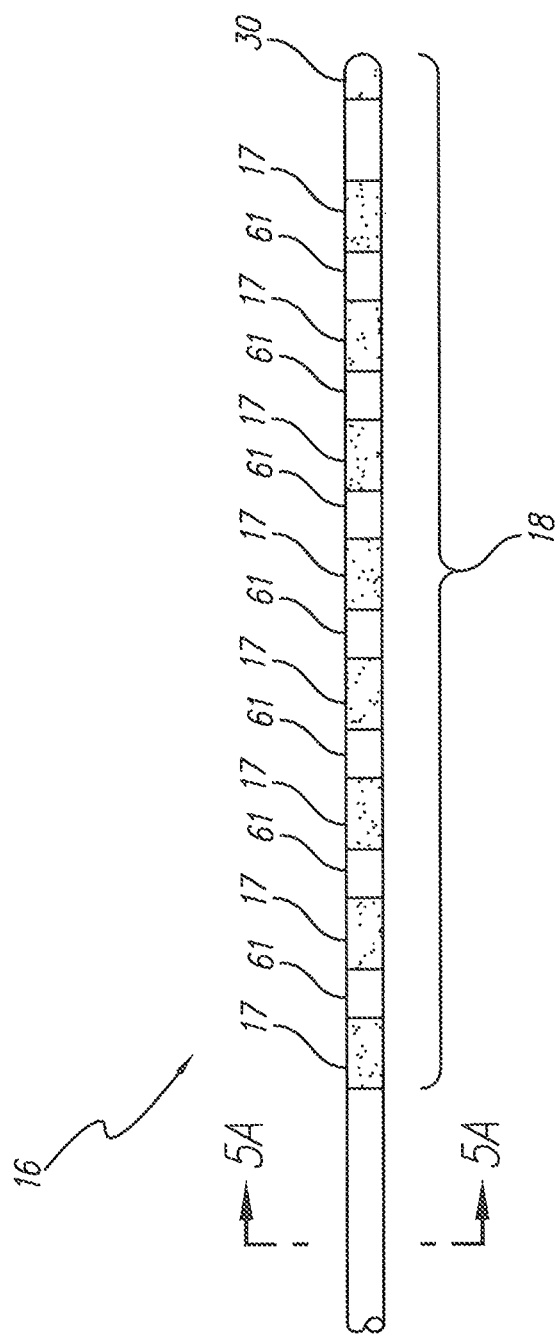

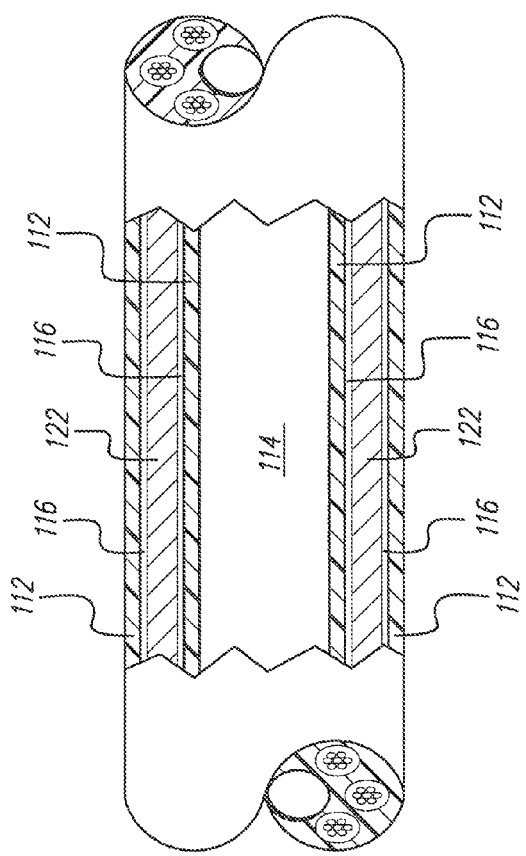
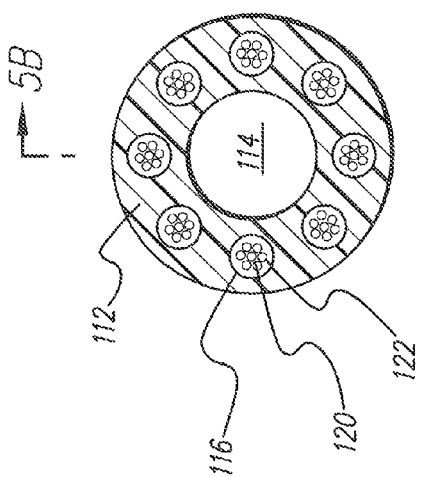
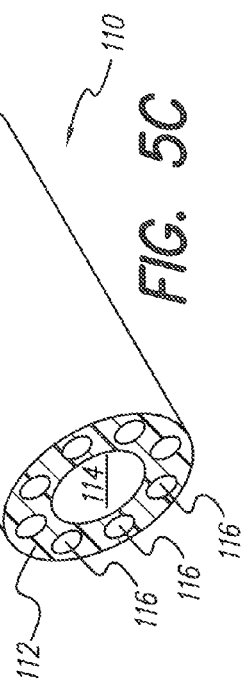

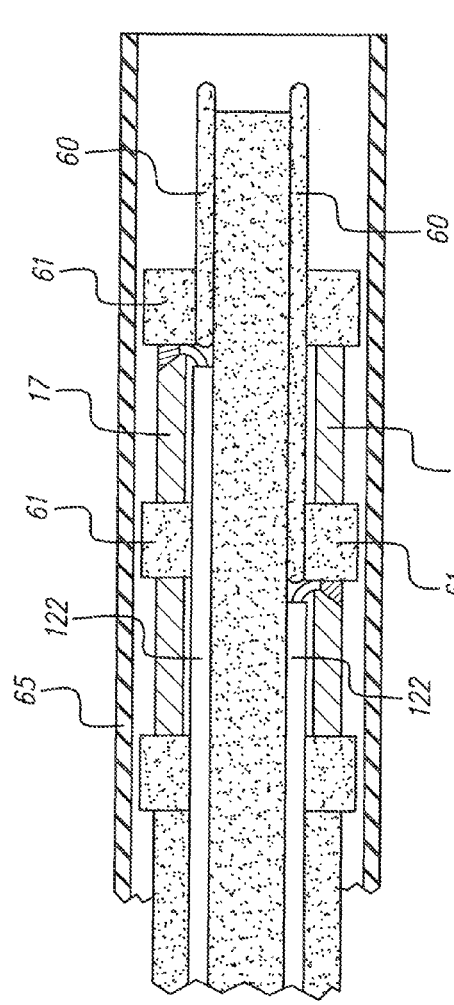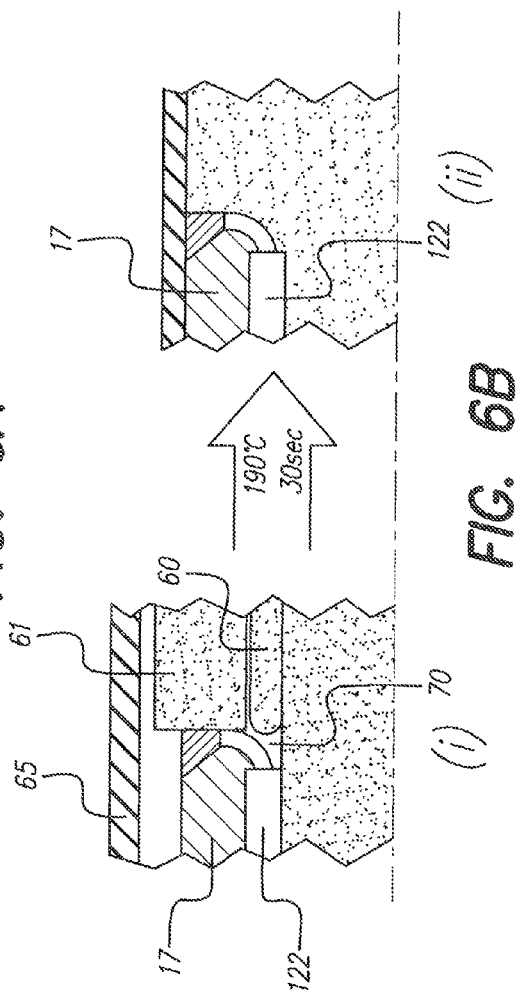

ELECTRODE ARRAY ASSEMBLY AND METHOD OF MAKING SAME

CROSS-REFERENCE TO RELATED APPLICATIONS

This utility patent application is a continuation of allowed U.S. patent application Ser. No. 11/329,907 filed Jan. 11, 2006, which claims the benefit of U.S. Provisional Patent Application Ser. No. 60/643,093, filed Jan. 11, 2005, all of which are herein incorporated by reference in their entirety.

FIELD OF THE INVENTION

The present invention relates to implantable leads for providing electrical stimulation and, more particularly, relates to leads having multiple electrode contacts and methods of making such leads.

BACKGROUND

Many types of implantable leads are currently used to treat a variety of maladies. Two common treatment applications use leads having multiple electrode contacts. Cochlear stimulator systems use a multiple electrode contact lead inserted into one of the cochlear chambers to stimulate the cochlear nerve. Another application where a multiple electrode contact lead is used is the treatment of chronic pain through stimulation of the spinal cord.

Spinal cord stimulation systems generally have two implantable components: an implantable pulse generator (IPG) and at least one lead connected to one output of the IPG. Generally, however, the IPG is a multi-channel device capable of delivering electrical current through the electrode contacts of the lead. The term "lead" used herein will refer to an elongate device having any conductor or conductors, covered with an insulated sheath and having at least one electrode contact attached to the elongate device, usually at the distal portion of the elongate device. The lead can have an inner stylet lumen running through most of the length of the lead and which lumen has an opening at the proximal end of the lead. A stylet may be placed into this stylet lumen during steering and implantation of the lead. The inserted stylet in the lumen can help stiffen the lead so that the stylet/lead combination may be more easily inserted through tissue.

There are two types of leads that may be used with the IPG. The first type is a paddle lead, which has a multiplicity of electrode contacts spread out over a flat, paddle-like surface that is attached to one end of the lead. A paddle lead advantageously permits the electrode contacts to be spaced apart to provide wide coverage over a stimulation area. A disadvantage presented with a paddle lead is that it usually requires a laminectomy or laminotomy, which are highly invasive surgical procedures necessary to implant the large, non-isodiametric paddle.

A second type of lead that is commonly used is a percutaneous lead, which has multiple electrode contacts positioned along the distal portion of an elongate lead. U.S. Pat. No. 6,205,361 issued to Baudino et al. describes the making of a multi-contact electrode array for a lead. The distal end of the lead may be about the same thickness or diameter as the remainder of the lead. The percutaneous lead is dimensionally configured for tunneling to a target stimulation site. No invasive surgical procedure such as a laminotomy is required; the percutaneous lead may be placed through an epidural type needle reducing surgical trauma.

The method of making a multi-contact percutaneous lead can be involved. In general, it is desirable to make the lead efficiently, with the fewest number of process steps, maximize the manufacturing yield, and hence reduce the cost of goods of building the leads. There is thus a continual need to improve the design of a percutaneous lead in order to improve its performance and to improve the method of manufacturing the lead.

BRIEF SUMMARY

A method of making a lead is provided. In one embodiment of the invention the method comprises: providing a plurality of conductive contacts located at the distal end of the stimulation lead; connecting a conductor wire to each of the conductive contacts; placing spacers between pairs of adjacent conductive contacts; placing monofilament within void spaces not occupied by a conductor wire, wherein the monofilament is the same material as the spacers; placing a heat shrink tubing around the spacers, conductive contacts and monofilament; and heating the spacers and monofilament just below the melting temperature to cause thermal fusion between the monofilament and spacer.

The conductive contacts may be connector contacts located at the proximal portion of the lead, which contacts are used to connect to the IPG, or the conductive contacts may be electrode contacts located somewhere on the lead (e.g., usually at the distal end of the lead).

In another embodiment of the method of making the lead, the method comprises: providing a plurality of conductive contacts located at the proximal end of the stimulation lead; connecting a conductor wire to each of the conductive contacts; placing spacers between pairs of adjacent conductive contacts; placing monofilament within void spaces not occupied by a conductor wire, wherein the monofilament is a different material than the spacers; placing a heat shrink tubing around the spacers, conductive contacts, and monofilament; and heating the spacers and monofilament to a temperature to cause thermal flow or melting of at least one of the spacers or monofilament.

Hence, while the monofilament and spacers may be the same material with the same melting temperatures, that is an optional part of the invention. The monofilament and spacers may actually be different materials, e.g., a type of thermoplastic polyurethane monofilament and another type thermoplastic polyurethane spacer, with different hardness and melting points in order to yield a particular stiffness.

In an embodiment of the invention, a lead assembly is provided comprising: a plurality of electrically conductive contacts; spacers placed between each adjacent contacts; a conductor wire connected to each conductive contact; and monofilament placed into void spaces not occupied by conductor wire, wherein the monofilament is made from the same insulative material as the spacer; and wherein the spacer and monofilament are thermally fused from heat applied to the lead assembly, which heat is just below the melting temperature of the spacer and the monofilament material.

In yet another embodiment, a lead assembly is provided comprising: a plurality of electrically conductive contacts; spacers placed between each adjacent contacts; a conductor wire connected to each conductive contact; and monofilament placed into void spaces not occupied by conductor wire, wherein the monofilament is made from a different insulative material as the spacer; and wherein the spacer and monofilament are heated to a temperature to cause either the spacer or monofilament material to thermally reflow or melt.

The monofilament and spacer may be the same thermoplastic material to have the same melting point and to thereby allow thermal fusion upon heating at a temperature just below the melting temperature of the material or the monofilament and spacer may have different melting points.

BRIEF DESCRIPTION OF THE DRAWINGS

The above and other aspects of the present invention will be more apparent from the following more particular description thereof, presented in conjunction with the following drawings wherein:

FIG. 3A shows a side view of the distal end of a percutaneous lead.

FIG. 5A shows a cross-sectional view of the percutaneous lead shown in FIG. 3A at line 5A-5A;

FIG. 5B shows a cross-sectional view of the percutaneous lead shown in FIG. 5A along line 5B-5B;

FIG. 5C shows a perspective view of the lead body, having a central stylet lumen and surrounding smaller lumens for containing conductor wires;

FIG. 6A shows a close-up, partial, longitudinal view of the lead assembly at the distal portion of the lead; and FIG. 6B depicts how polyurethane monofilament or a thermoplastic material is used to fill the voids and is incorporated into the lead by applying heat.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figures 1, 2:
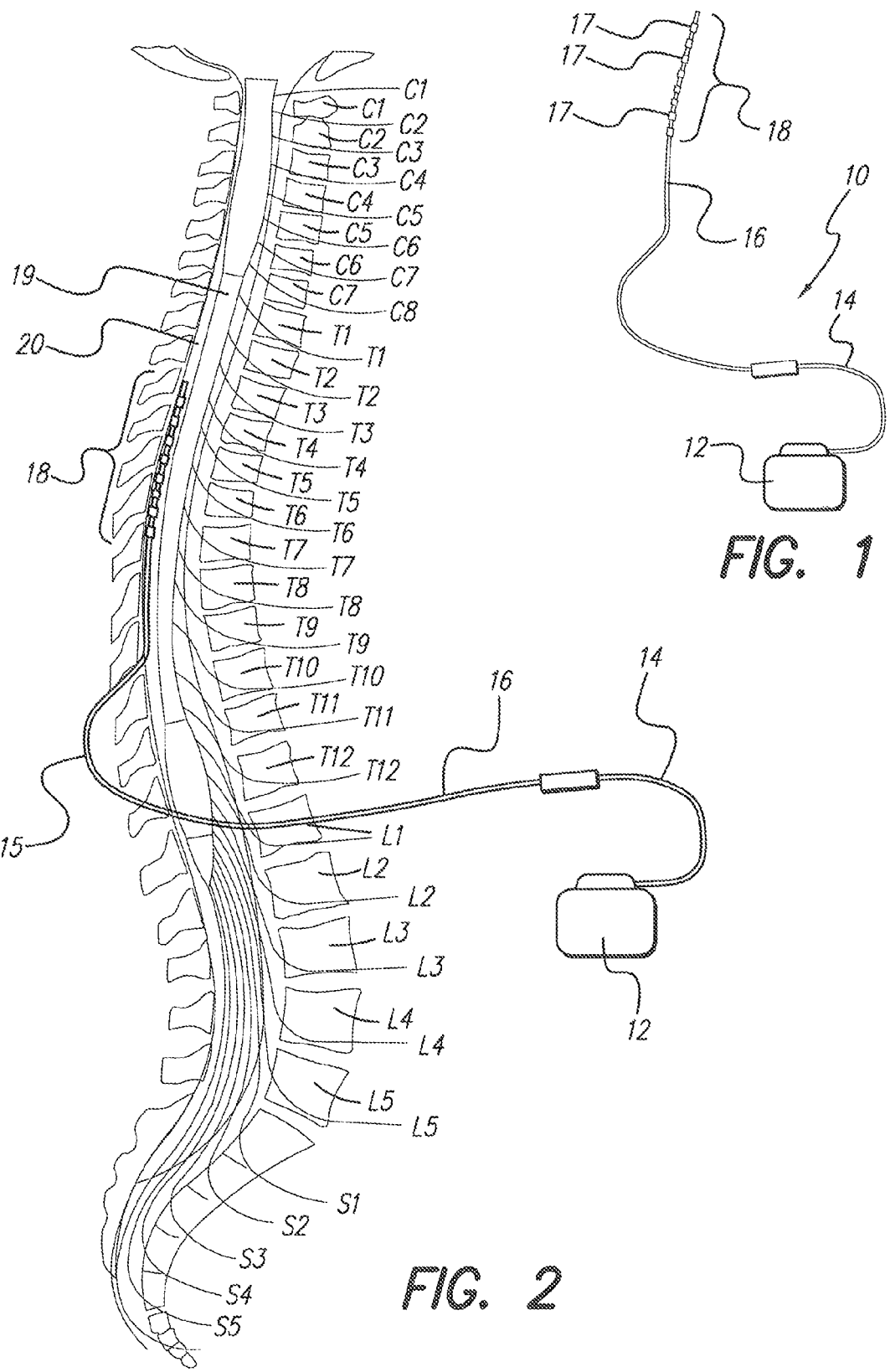
FIG. 1 shows a generalized spinal cord stimulation system with a percutaneous lead connected to an implantable pulse generator ("IPG")
FIG. 2 shows an illustration of the percutaneous lead implanted into the epidural space of a human spinal cord.

FIG. 1 shows a generalized stimulation system that may be used in spinal cord stimulation (SCS), as well as other stimulation applications. Such a system typically comprises an implantable pulse generator ("IPG") 12, an optional lead extension 14, a lead 16 and an electrode array 18. The electrode array 18 includes a plurality of electrode contacts 17. In a percutaneous lead, the electrode contacts 17 can be arranged in an in-line electrode array 18 at the distal end of the lead 16. Other electrode array configurations can also be used. The IPG 12 generates stimulation current pulses that are applied to selected electrode contacts 17 within the electrode array 18.

The proximal end of the lead extension 14 can be removably connected to the IPG 12 and a distal end of the lead extension 14 can be removably connected to a proximal end of the lead 16. The electrode array 18 is formed on a distal end of the lead 16. The in-series combination of the lead extension 14 and lead 16 conduct the stimulation current from the IPG 12 to electrode contacts 17 of the electrode array 18. It is noted that the lead extension 14 need not always be used with the neural stimulation system 10. Instead, the lead extension 14 may be used when the physical distance between the IPG 12 and the electrode array 18 requires its use, or for the purpose of a temporary trial procedure.

The IPG 12 contains electrical circuitry, powered by an internal primary (one-time-use-only) or a rechargeable battery, which through the use of electrical circuitry can output current pulses to each stimulation channel. Communication with the IPG can be accomplished using an external programmer (not shown), typically through a radio-frequency (RF) link.

FIG. 2 shows a transverse, mid-sagittal view of a spinal cord and a generalized, implantable, spinal cord stimulation system. The stimulation system shown is being used as a spinal cord stimulator (SCS) system. In such an application, the lead 16 and, more particularly, the electrode array 18 are implanted in the epidural space 20 of a patient in close proximity to the spinal. cord 19. Because of the lack of space near the lead exit point 15 where the electrode lead 16 exits the spinal column, the IPG 12 may be implanted in the abdomen or above the buttocks. Use of lead extension 14 facilitates locating the IPG 12 away from the lead exit point 15.

FIG. 3A shows, in accordance with the invention, a distal portion of a percutaneous stimulating lead 16. The stimulating lead 16 is used to stimulate neural tissue by delivering electrical stimulus pulses through at least one of the electrode contacts 17. The electrode contacts 17 can be separated by electrode contact spacers (or an insulative material) 61 that insulate the electrode contacts 17 from each other. A radiopaque marker 30 located at the distal tip of the lead 16 may be optionally included. Alternatively, the tip of the lead may be the same material as the remainder of the lead insulation. The IPG 12 may be configured to permit connection to the two stimulating leads, each having eight electrode contacts 17. A pair of stimulating leads 16 may be connected to an IPG 12 and an electrical circuit may be created between one electrode contact on the first lead and another electrode contact located on the second lead. The IPG 12, for example, may have sixteen independently programmable outputs that allow programming of pulse amplitude, pulse width and frequency of the pulse width. The electrode contacts 17 are to be made of a bio-compatible, electrically conductive electrode material such as platinum/iridium alloy, platinum, titanium or the like.

As an example, the stimulating lead 16 may have a diameter of between about 0.03 to 0.07 inches for spinal cord stimulation applications. An insertion cannula (not shown), e.g., a 14 gauge insertion needle may be used, while a 0.05 inch diameter stimulating lead is inserted within the cannula to help implant the stimulating lead 16. The stimulating lead 16 may come in a variety of lengths, e.g., 30, 50, 70 and 90 cm. A practitioner can extend the length of any of the available lead lengths by opting to use an extension lead 14 (shown in FIG. 1). The proximal male end of the extension lead 14 should be configured to be insertable into the lead connector of the IPG and the distal female end of the extension lead should be configured to accept the proximal connector end of the stimulating lead 16.

Figure 3B:
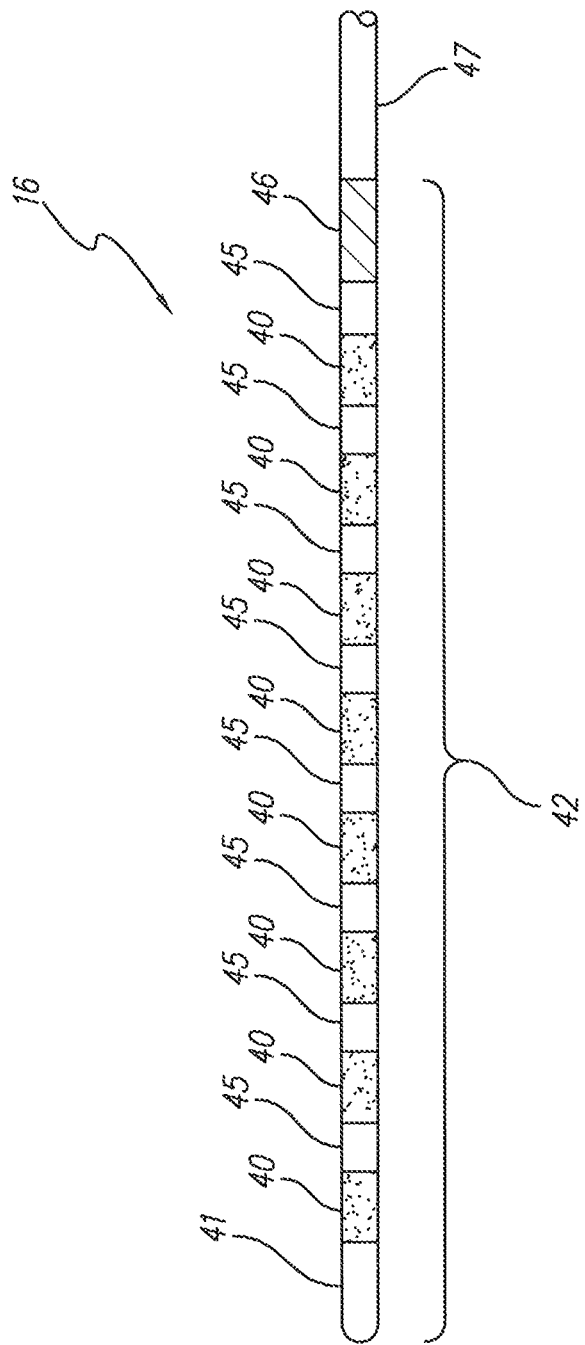
FIG. 3B shows a side view of the proximal (connector) end of the percutaneous lead shown in FIG. 3A.

FIG. 3B shows, in accordance with the invention, a depiction of the proximal end of the lead 16. This proximal lead end, including the eight, electrically conductive, connector contacts 40, and a contact tip element 41, collectively will be called herein as the proximal lead connector end 42 of the stimulating lead 16. Connector contact spacers 45 are placed between the connector contacts 40. The spacers 45 may be made from an implantable grade polyurethane such as Pellethane® 55D thermoplastic material. The contacts 40 may be made from a non-corrosive, electrically conductive material, e.g., platinum/iridium alloy or platinum. Contact tip 41, however, is not electrically connected to any conductor and contact tip 41 may merely serve as a hard surface for a mechanical contact securing device, such as a set screw, which may be used to secure the lead connector end 42 with the connector block of the IPG 12. Contact tip 41 is optional and does not need to be included as part of the lead. Instead, the contact tip of the lead may be of similar or the same insulation material as the remainder of the lead 16 or lead body 110 (FIG. 5C).

Preferably the lead 16 is substantially isodiametric, meaning that the diameter along the lead's entire length is equal or nearly equal. However, the lead 16 does not need to be isodiametric. For example, the connector contacts 40 at the proximal end may be larger (oversized) or smaller in diameter compared to the remainder of the lead 16 or lead body 110 (shown in FIG. 5C). Likewise, the electrode contacts 17 may be larger (oversized) or smaller in diameter compared to the remainder of the lead 16 or lead body 110 (shown in FIG. 5C).

Figure 4:
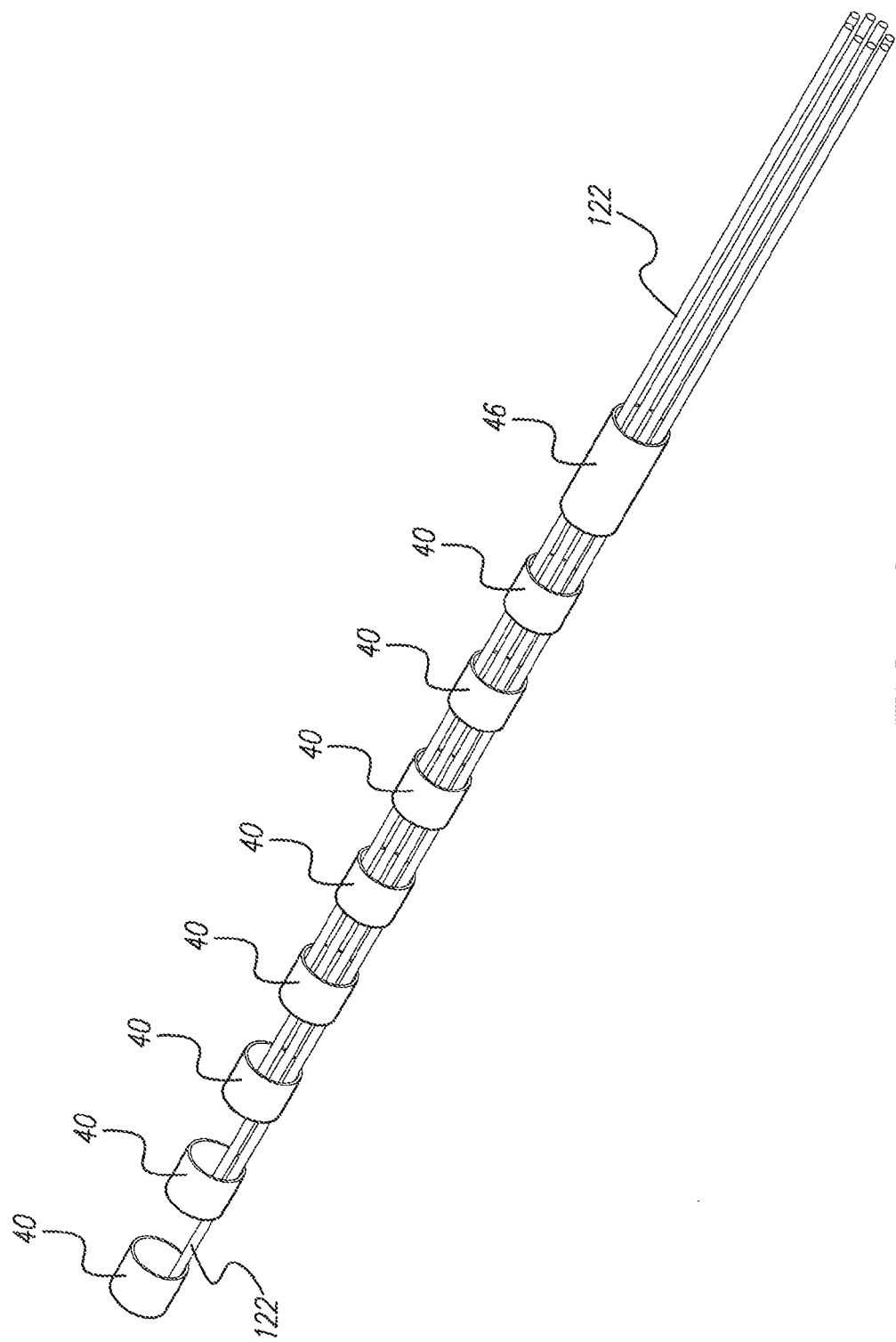
FIG. 4 shows a view of the proximal end of the lead assembly showing the connector contacts and conductor wires that connect to each connector contact.

FIG. 4 shows a proximal lead assembly with each of the connector contacts 40 welded to a respective one of conductors 122. Each of the eight connector contacts 40, as shown, are connected to a conductor 122 which, in turn, are connected to a respective electrode contact 17 at the distal end of the stimulating lead 16. The insulating material between the connector contacts 40 and around the conductors 122 is not shown in FIG. 4 for purposes of better illustrating the connection between each conductor and its respective connector contact. The connection may be a weld. Cylindrical element 46 is optional and is not connected to any conductor. Cylindrical element 46 may be used as a contact element for a mechanical securing device such as a set screw in order to secure the lead 16 to the IPG 12. Alternatively, or in addition, the cylindrical element 46 may function as a radiopaque element, provided that the material used for element 46 is radiopaque.

FIG. 5A shows a cross-sectional view of the lead of FIG. 3A along line 5A-5A.

FIG. 5B shows a partial, cross-sectional view of the lead along the line 5B-5B.

FIG. 5C shows a perspective view of an exemplary lead body 110 of the lead 16, excluding conductor wires. The lead body is that portion of the lead insulation 112 that is between the distal electrode contact array 18 and the array of connectors contacts 40 (FIG. 4) at the proximal lead connector end 42. The lead body 110 may be extruded as a one-piece component. Note the central stylet lumen 114 and the surrounding eight conductor lumens 116.

FIGS. 5A and 5B show an exemplary embodiment of an insulation section 112 of the lead body 110 having eight lumens 116 containing the conductor (wires) 122, having individual strands 120. For example 15 or 16 individual conductor strands 120 may be braided or bundled into a single conductor 122. Also shown is a central lumen 114 that may be used to accept an insertion stylet (not shown) within the lumen to facilitate lead implantation. The opening of the lumen occurs at the proximal end of the lead 16. The lead body 110 may be a biocompatible, insulating lead material. Preferably the lead body 110 is made from a polyurethane. In particular the material may be Pellethane® thermoplastic material, e.g. 55D, 65D, or other durometer hardness. As previously indicated for FIG. 5C, the lead body 110 shown in FIG. 5B may be extruded as one piece.

FIG. 6A shows a partial view of a longitudinal, cross-section at the distal end of the lead, in accordance with an embodiment of the invention. FIG. 6A shows a ring-like electrode contact 17 (which may be platinum, for example), multi-stranded conductor 122 and electrode contact spacer 61 (or an insulative material). The spacer 61, which is ring-like in configuration, may be made of polyurethane insulative material, e.g., Pellethane®. Monofilament 60, also may be made of thermoplastic Pellethane® material or other insulation material, e.g., polyester. During manufacture, the monofilament 60 may be inserted into the void spaces that are not filled by the conductor 50. A heat shrink tube 65 is also shown placed around the electrode contacts 17 and conductor 122 assembly. The heat shrink tube 65 may be PTFE (e.g., Teflon® material) or a polyester heat shrink material. The heat shrink tube can be used during manufacturing and is not part of the stimulation lead.

FIG. 6B shows a two-frame, time-elapsed illustration of a partial view of the distal end of the lead as in FIG. 6A showing the conductor 122 connected (e.g., welded) to the electrode contact 17. The first frame (i) of FIG. 6B shows the sequence in which the monofilament 60 fills a large part of the void space 70. The part of the lead assembly shown is then placed into a heat, for example, at 190 degrees Celsius for a period of 30 seconds. The heat that may be used, e.g., for polyurethane material (such as Pellethane®), may range from about 140 to 250 degrees Celsius for a period of about between 15 to 120 seconds. However, importantly, the heat applied to the spacer and monofilament material, should be just below the melting temperature of the material. At this just-below-melting temperature, the spacer and monofilament will reflow and thermally fuse together as shown in the second frame (ii). The spacer 61 and the monofilament 60 may be exactly the same material with the same melting temperature in order to facilitate thermal fusion. For example, the material may be the same implantable grade polyurethane such as Pellethane 55 D or 75 D.

Alternatively, however, the monofilament may be of a different material than the spacer to alter the mechanical characteristic of the final lead assembly. The monofilament and spacer may have different melting points or very close melting points. The monofilament and spacers may be the same type of material but with different formulations, e.g., to provide different hardness. For example, the monofilament may be a 55 D (durometer hardness) material and the spacer may be a 75 D material. The predetermined temperature chosen to heat both the monofilament and spacers should cause at least one of the materials used to thermally reflow or, alternatively to melt. In some cases, the temperature may be chosen that one material melts while the other material thermally reflows.

While FIGS. 6A and 6B show the distal end of the lead, the same process of using a monofilament to fill up void spaces may be used at the proximal end of the lead assembly. At the proximal end of the lead assembly, the conductive contacts are not electrode contacts but, are instead, electrically conductive connector contacts 40 that must be in electrical connection with complementary contacts in the IPG connector. The connector contact spacers 45 at the proximal end of the lead (shown in FIG. 3B) are placed between adjacent connector contacts 40. In one embodiment of the invention, the connector contact spacers 45 may be oversized—that is, the spacers may have an initial diameter that is larger than the final lead diameter. The proximal connector end of the lead assembly 42 may then be heated to a temperature (just below melting point of the spacer and monofilament) for a duration of time previously described in order to produce thermal fusion of the connector contact spacer 45 and monofilament 60 to create a continuous reflow of material between the spaces not occupied by the connector contacts 40 and conductor wires 122.

Alternatively, the monofilament 60 and spacer 45 may be different materials with different melting points or about the same melting points.

Hence, the method of placing monofilament into void spaces not occupied by the conductor 122, may be used solely at the distal end of a lead, solely at the proximal end of a lead, or may be employed concurrently at both ends of a lead. If only one end of a lead employs monofilament, the other end of the lead may employ another method to finish the build, e.g., overmolding using a mold or injecting material such as epoxy, e.g., Hysol® into the void spaces between the contacts and conductor wires.

EXAMPLE

The following steps illustrate one example embodiment of a method for making the lead, in accordance with the invention. Embodiments of the method can include one or more of the following steps (although not necessarily in the order presented). (1) A braided or bundled, insulated, multi-filament conductor, e.g., having 2-200 filaments, can be ablated of insulation at one end to expose the conductor. (2) The exposed end of the conductor can be welded to an electrode contact (located on the distal end lead assembly). (3) Oversized, distal lead spacers may be placed between the electrode contacts. (4) The multi-lumen tube (lead body) may be pre-cut with ablated section located at the distal and proximal ends. (5) Each end of the conductor cable can be inserted through the corresponding conductor lumens in the lead body. (6) The oversized spacers can be placed between each ring-like electrode contact at the distal end of the lead assembly; the spacers 61 may be "oversized", meaning that they may have a diameter greater than the lead body 110 and in addition, the diameter of the electrode contacts 17 may be oversized compared to the diameter of the lead body 110. (7) The distal end of each conductor cable can be welded to the ring-shaped electrode contact. (8) Polyurethane monofilament may be placed inside the void space as shown in FIG. 6A, and inside any empty conductor lumens 116. (9) A heat shrink tube or wrap, preferably, made from PTFE (Teflon) or polyester, can be placed over the distal end of the lead assembly and over the electrode array; this distal end can be placed into a high temperature block, e.g., between about 140-250 degrees Celsius for a period of about 30 to 120 seconds. (10) The distal assembly can be removed from the heat and the shrink tube or wrap can be removed. (10) Optionally, the distal tip of the lead can be formed using an RF welder.

Post processing of the lead is not always required. For example, grinding of the distal or proximal ends of the leads is not necessary with this method of manufacturing, although optionally, a centerless grinding process may be used, if desired.

The method of making the distal and proximal part of the lead, in accordance with the present invention, eliminates most, if not all tooling, including eliminating the use of molds.

The method of making a lead and the resulting multi-contact lead, in accordance with the invention, provides advantages over conventional leads and methods of making a lead. A prior method of making the distal portion of the lead uses epoxy to fill the voids between the spacer 61 and the contacts 17. This has certain disadvantages. For instance, use of an epoxy requires a curing step, e.g., of up to eight hours, adding to the total time required to build a lead. With use of epoxy, there may also be some variation in stiffness of the final lead assembly post-cure because the epoxy is generally a different material than the insulative body or spacers and because curing may occur unevenly. The use of like materials, e.g., polyurethane lead body, polyurethane spacers and polyurethane monofilament can yield a better bond between these parts.

Although the lead and method of making the lead are described in the context of a spinal cord stimulation lead, it will be understood by those skilled in the art that the same lead, albeit with appropriate dimensions for a particular application, and the method of making the lead may be used to make a multi-contact lead suitable for use in other applications, such as deep brain stimulation, cardiac stimulation and peripheral nerve stimulation.

While the invention herein disclosed has been described by means of specific embodiments and applications thereof, numerous modifications and variations could be made thereto by those skilled in the art without departing from the scope of the invention set forth in the claims.

What is claimed and desired to be protected by Letters Patent of the United States is:

1. A method of manufacturing a stimulation lead comprising:
providing a lead body comprising an insulation section, the insulation section defining a central lumen extending along the insulation section and a plurality of conductor lumens extending along the insulation section and arranged around, and external to, the central lumen, the lead body further comprising a plurality of conductive contacts located along an axial end of the lead body, and a plurality of conductor wires, wherein each of the conductor wires is disposed within one of the plurality of conductor lumens and each of the conductor lumens of the plurality of conductor lumens has at least one of the conductor wires of the plurality of conductor wires disposed therein, wherein a portion of the conductor lumens is disposed radially beneath the conductive contacts;
after providing the lead body, conductively coupling at least one of the plurality of conductor wires to each of the conductive contacts; and
after providing the lead body, placing non-conductive material into a portion of at least one of the conductor lumens of the lead body, wherein at least a portion of the non-conductive material is disposed radially beneath the conductive contacts.

2. The method of claim 1, further comprising heating the non-conductive material to cause the non-conductive material to thermally reflow or melt.

3. The method of claim 1, wherein placing non-conductive material comprises placing the non-conductive material into a portion of each of the conductor lumens of the lead body, wherein at least a portion of the non-conductive material in each of the conductor lumens is disposed radially beneath the conductive contacts.

4. The method of claim 1, further comprising placing spacers between pairs of adjacent conductive contacts.

5. The method of claim 4, further comprising heating the non-conductive material and spacers to cause the non-conductive material to thermally reflow or melt and to cause the non-conductive material and spacers to thermally fuse together.

6. A method of manufacturing a stimulation lead comprising;
providing a lead body comprising a insulation section, the insulation section defining a central lumen extending along the insulation section and a plurality of conductor lumens extending along the insulation section and arranged around, and external to, the central lumen, the lead body further comprising a plurality of conductive contacts located along an axial end of the lead body, and a plurality of conductor wires, wherein each of the conductor wires is disposed within one of the plurality of conductor lumens and each of the conductor lumens of the plurality of conductor lumens has at least one of the conductor wires of the plurality of conductor wires disposed therein, wherein a portion of the conductor lumens is disposed radially beneath the conductive contacts;

after providing the lead body, conductively coupling at least one of the plurality of conductor wires to each of the conductive contacts;

after providing the lead body, placing non-conductive material into a portion of at least one of the conductor lumens of the lead body, wherein at least a portion of the non-conductive material is disposed radially beneath the conductive contacts; and after placing the non-conductive material, heating the non-conductive material at a temperature in a range of 140 to 250 degrees Celsius for a period in a range of 15 to 120 seconds to cause the non-conductive material to thermally reflow or melt.

7. The method of claim 6, wherein the plurality of conductor lumens is exactly eight conductor lumens.

8. The method of claim 6, wherein placing non-conductive material comprises placing the non-conductive material into a portion of each of the conductor lumens of the lead body, wherein at least a portion of the non-conductive material in each of the conductor lumens is disposed radially beneath the conductive contacts.

9. The method of claim 6, further comprising placing spacers between pairs of adjacent conductive contacts.

10. The method of claim 9, wherein heating the non-conductive material comprises heating the non-conductive material and spacers to cause the non-conductive material to thermally reflow or melt and to cause the non-conductive material and spacers to thermally fuse together.

11. The method of claim 6, wherein the non-conductive material comprises polyurethane.

* * * * *